United States Patent
Hougland et al.

(10) Patent No.: US 9,115,383 B2
(45) Date of Patent: Aug. 25, 2015

(54) FLUORESCENCE ASSAY FOR GHRELIN O-ACYLTRANSFERASE ACTIVITY

(71) Applicants: James Hougland, Fayetteville, NY (US); Joseph Darling, Liverpool, NY (US)

(72) Inventors: James Hougland, Fayetteville, NY (US); Joseph Darling, Liverpool, NY (US)

(73) Assignee: Syracuse University, Syracuse, NY (US)

(*) Notice: Subject to any disclaimer, the term of this patent is extended or adjusted under 35 U.S.C. 154(b) by 0 days.

(21) Appl. No.: 14/046,131

(22) Filed: Oct. 4, 2013

(65) Prior Publication Data

US 2014/0212904 A1    Jul. 31, 2014

Related U.S. Application Data

(60) Provisional application No. 61/709,346, filed on Oct. 4, 2012.

(51) Int. Cl.

| | |
|---|---|
| *C12Q 1/48* | (2006.01) |
| *C12N 9/00* | (2006.01) |
| *C12N 9/10* | (2006.01) |
| *C12N 1/20* | (2006.01) |
| *C12N 15/00* | (2006.01) |
| *C07H 21/04* | (2006.01) |

(52) U.S. Cl.
CPC ............... *C12Q 1/48* (2013.01); *C12N 9/1029* (2013.01); *G01N 2333/91051* (2013.01)

(58) Field of Classification Search
None
See application file for complete search history.

(56) References Cited

PUBLICATIONS

Chica et al. Curr Opin Biotechnol. Aug. 2005;16(4):378-84.*
Sen et al. Appl Biochem Biotechnol. Dec. 2007;143(3):212-23.*
Accession B3KZ06. Sep. 2, 2008.*
Accession Q4YGF5. Jul. 5, 2005.*
Amanda L. Garner and Kim D. Janda, A small molecule antagonist of ghrelin O-acyltransferase (GOAT), The Royal Society of Chemistry 2011, ChemComm, Chem. Commun.,2011, 47, 7512-7514.

* cited by examiner

*Primary Examiner* — Christian Fronda
(74) *Attorney, Agent, or Firm* — David L. Nocilly; George R. McGuire; Bond Schoeneck & King, PLLC

(57) ABSTRACT

An assay to detect ghrelin O-acyltransferase activity using an acrylodan-labeled peptide mimic of ghrelin that provides for high-throughput screening for ghrelin O-acyltransferase inhibitors and detection via high performance liquid chromatography. Alternatively, the assay for ghrelin acylation may be based on a synthetic peptide substrate that mimics the N-terminal sequence of ghrelin and has an environmentally-sensitive fluorophore attached to its C-terminal amino acid through chemoselective ligation.

8 Claims, 5 Drawing Sheets

FLUORESCENCE ASSAY FOR GHRELIN O-ACYLTRANSFERASE ACTIVITY

CROSS-REFERENCE TO RELATED APPLICATIONS

The present application claims priority to U.S. Provisional Application No. 61/709,346, filed on Oct. 4, 2012.

BACKGROUND OF THE INVENTION

1. Field of the Invention

The present invention relates to assays for ghrelin O-acyltransferase activity and, more particularly, to a substrate and assay for detecting ghrelin modification by ghrelin O-acyltransferase.

2. Description of the Related Art

The ghrelin-ghrelin O-acyltransferase (GOAT) system has been implicated as a potential target for pharmacologic modulation of a number of disorders, including obesity and diabetes. Ghrelin is a peptide hormone involved in appetite regulation, glucose metabolism, and also potentially learning and memory. To transduce ghrelin-dependent signaling, ghrelin requires octanoylation of its serine 3 residue (GSS-FLS . . . ) (SEQ. ID No. 1) to bind and activate its cognate receptor. This acylation is catalyzed by ghrelin O-acyltransferase (GOAT), a member of the MBOAT family of integral membrane enzymes.

With ghrelin impacting multiple physiological pathways, the ghrelin-GOAT system presents an attractive therapeutic target. For example, ghrelin-linked signaling may be involved in various problems, such as obesity, appetite regulation, type II diabetes, and other conditions, as well as involved in learning and memory, depression, and Parkinson's disease. However, the lack of information regarding GOAT structure and catalytic mechanism renders GOAT inhibitor design and optimization difficult.

BRIEF SUMMARY OF THE INVENTION

The present invention comprises a substrate and an assay for human ghrelin O-acyltransferase activity. The first step of an assay according to the present invention is to design a synthetic peptide substrate that mimics the N-terminal sequence of ghrelin. The next step in the present invention is to attach an environmentally-sensitive fluorophore to the C-terminal amino acid of the substrate through chemoselective ligation. Then, upon octanoylation of serine 3, the peptide substrate becomes more hydrophobic, leading to an increase in the fluorescence of the environmentally-sensitive fluorophore. Alternatively, the presence of any acylation of the fluorescent peptide substrate can be detected via reverse-phase high performance liquid chromatography (HPLC).

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 3:
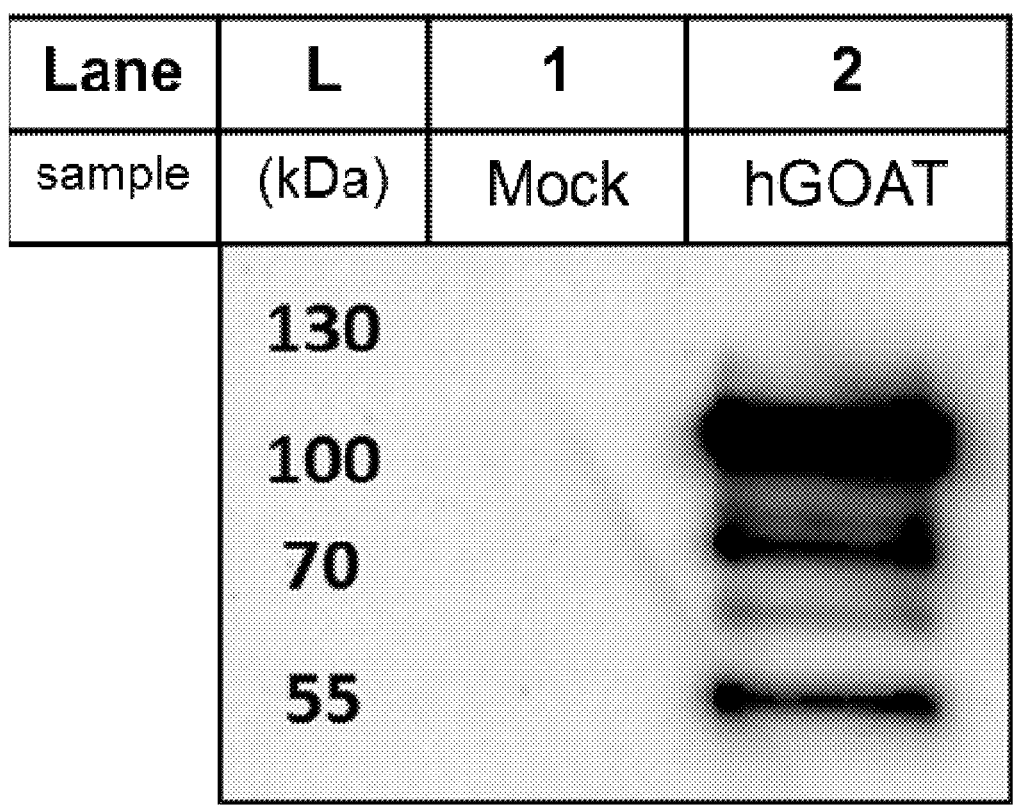

FIG. 3 is a schematic of ghrelin peptide acylation reactions with the fluorescent GSSFLC$_{AcDan}$ substrate, where (A) is a reaction with control/mock membrane fraction; (B) is a time course for GSSFLC$_{AcDan}$ acylation using GOAT membrane fraction, and where the assays were incubated for 1-10 minutes at 37° C. and all reactions were analyzed using reverse-phase HPLC under the following assay conditions: 10 µM peptide, 50 µg membrane protein, 500 µM octanoyl coenzyme A, 100 µM palmitoyl coenzyme A, 50 mM HEPES buffer pH 7.0.

Figure 4:

FIG. 4 is a schematic of the analysis of N-terminal and S2 selectivity of hGOAT.

Figure 5:
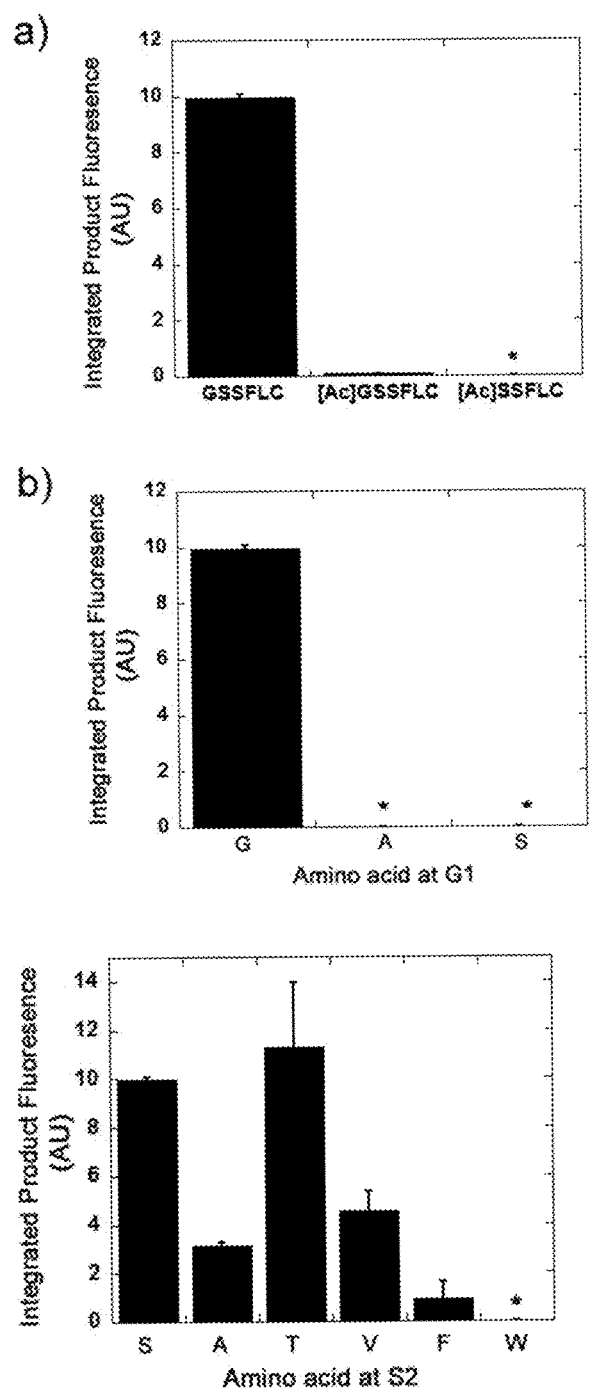

FIG. 5 is a series of graphs showing the functional characteristics of substrates recognized by hGOAT.

DETAILED DESCRIPTION OF THE INVENTION

Figure 1:
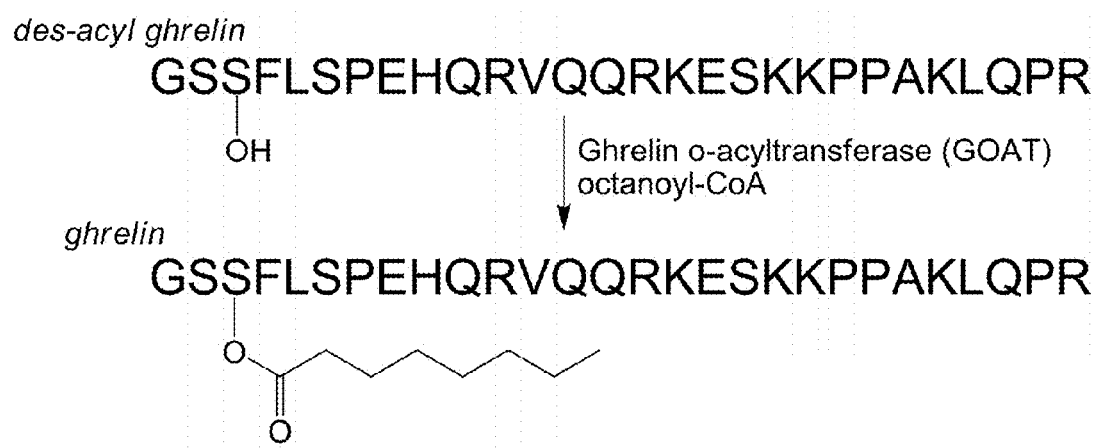
FIG. 1 is a schematic of ghrelin acylation by ghrelin O-acyltransferase.

The present comprises a fluorescence-based assay for ghrelin acylation that greatly simplifies mechanistic studies of GOAT and allows for high-throughput screening of potential GOAT inhibitors. As seen in FIG. 1, GOAT catalyzes the n-octanoyl transfer to ghrelin. Only acylated ghrelin binds to its cognate receptor and a large fraction of ghrelin species in circulation is des-acyl ghrelin. GOAT-catalyzed acylation thus potentially serves as a mechanism for controlling ghrelin-mediated signaling.

The first step of an assay according to the present invention is to design one or more synthetic peptide substrates that mimic the N-terminal sequence of ghrelin. The next step in the present invention is to attach an environmentally-sensitive fluorophore to the C-terminal amino acid of the substrate through chemoselective ligation. Then, upon octanoylation of serine 3 of ghrelin by GOAT, the peptide substrate becomes more hydrophobic leading to an increase in the fluorescence of the environmentally-sensitive fluorophore and increased peptide substrate retention time on reverse-phase HPLC.

In order to test the activity of peptide substrates, the gene for hGOAT was cloned with a C-terminal His10 tag into the pFastBacDual vector and expressed using standard baculoviral procedures.

Figure 2:
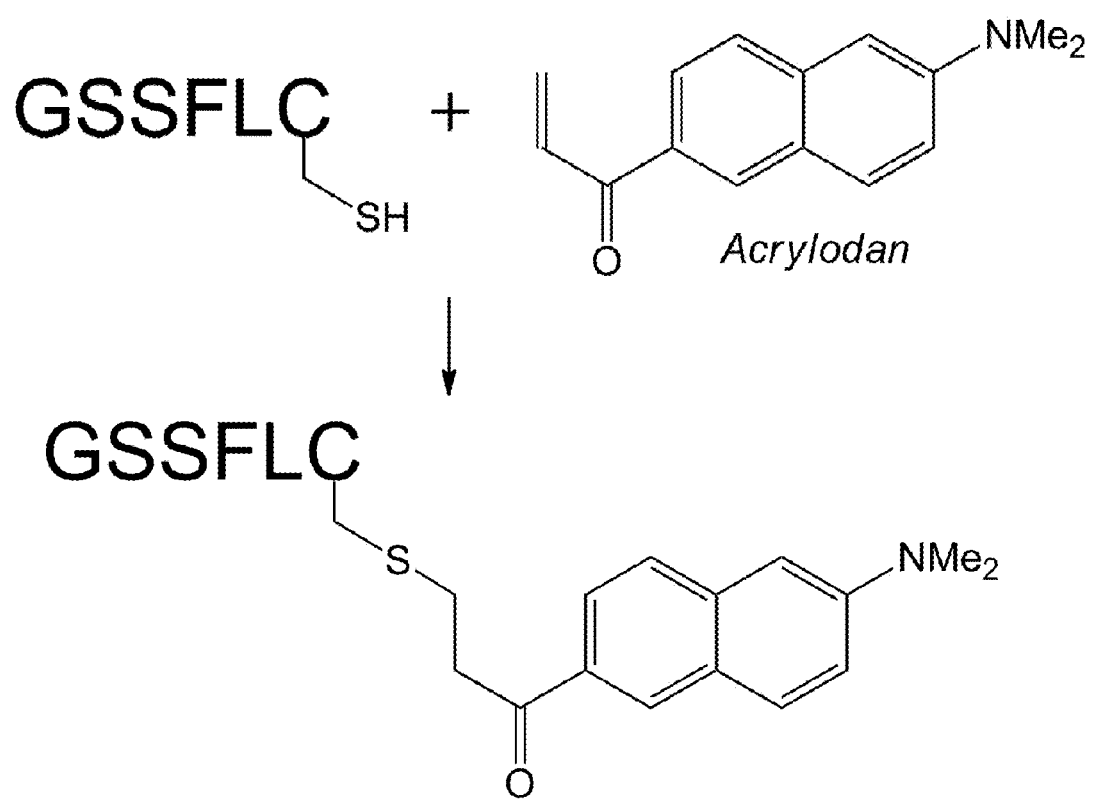
FIG. 2 is a schematic of a fluorescently labeled ghrelin fragment according to the present invention.

As seen in FIG. 2, an exemplary peptide substrate for evaluating GOAT-catalyzed acylation was created by forming an acrylodan (AcDan) labeled fragment of the ghrelin peptide. A series of ghrelin mimic peptides were created along these lines with covalently attached fluorophores to serve as fluorescent substrates according the present invention, and tested for activity with hGOAT, as detailed in Table 1 below.

TABLE 1

Peptide substrates for fluorescence-based assay of GOAT activity

| Sub-strate | Peptide Sequence | Active with hGOAT? |
|---|---|---|
| 1-Dansyl | Dansyl-GSSFLS (SEQ. ID No. 2) | No |
| AcDan-2 | GC$_{AcDan}$SFLS (SEQ. ID No. 3) | No |
| AcDan-5 | GSSFC$_{AcDan}$S (SEQ. ID No. 4) | Yes |
| AcDan-6 | GSSFLC$_{AcDan}$ (SEQ. ID No. 5) | Yes |

It should be recognized by those of skill in the art that other environmentally sensitive fluorophores (including, but not limited to, dansyl, dapoxyl, coumarin fluorophores) may be employed. Alternatively, fluorophore coupling chemistry may be used to develop fluorescent ghrelin analog substrates with higher reactivity and fluorescence yields.

The peptides are derived from the N-terminal sequence of ghrelin (GSSFLS) (SEQ. ID No. 1) and include all amino acids currently proposed to be important for ghrelin recognition by GOAT. The dansyl and acrylodan (AcDan) fluorophores used exhibit fluorescence enhancement upon a change in the polarity of the local environment, such as the increase in hydrophobicity expected upon octanoylation of serine 3 of ghrelin by hGOAT. Similar assays have proven robust for studying protein prenylation, another form of protein lipidation. The cysteine mutations at positions 2, 5, and 6 allow for AcDan conjugation at these sites, with mutations targeted to residues that are suggested to be non-essential for GOAT recognition. Fluorophore attachment was confirmed by HPLC and MALDI mass spectrometry, and milligram quantities of purified fluorescently labeled peptides may be produced.

With the peptide substrates, the addition of the hydrophobic octanoyl group upon serine acylation at position 3 leads to an increase in retention time in reverse-phase (RP) HPLC. The panel of fluorescent ghrelin peptide substrates was assayed for activity with hGOAT using HPLC coupled with fluorescence detection of the fluorescently labeled peptides. All reactions with hGOAT-His 10 membranes were performed in parallel with mock membranes to account for non-specific peptide modifications. Substrates with fluorophores attached N-terminal to the octanoylation site at serine 3 (1-Dansyl and AcDan-2) were not modified by hGOAT, whereas reactions with both the AcDan-5 and AcDan-6 substrates yielded the octanoylated peptide with increased retention time, as seen in FIG. 4.

The peptide substrates were further used to study hGOAT selectivity at the N-terminus, the N-terminal glycine 1(G1) side chain and the serine 2(S2) positions, as seen in FIG. 5. For example, acetyl mutants at the N-terminus of the ghrelin mimic remove the charged N-terminal amine of the ghrelin peptide. Alanine and serine mutants at the G1 position introduce a gradual incline in steric bulk at the glycine-H side chain. Finally, S2 mutants increase gradually in size, whilst also testing for importance of the hydroxyl group on the serine side chain (Ser→Ala, Thr→Val).

Referring to FIG. 5, the results of studies using the peptide substrates shed light on the functional characteristics of substrates recognized by hGOAT. These results indicate the importance of the charged N-terminal amine in recognition by hGOAT ([Ac]GSSFLC (SEQ. ID No. 1) exhibits low activity, [Ac]SSFLC (SEQ. ID No. 6) shows no activity). Interestingly, threonine showed an equal and perhaps even higher activity than serine in the S2 series, indicating the hydrogen bonding capability of this side chain might be essential for recognition. Beyond phenylalanine, there was no observed activity with tryptophan, a larger amino acid side chain.

These studies expose previously unknown characteristics regarding the active site of hGOAT, which gives a clearer picture of what chemical properties may be crucial regarding hGOAT substrate discrimination. For example, the N-terminal amine appears to be essential for hGOAT identification. Results for the G1 side chain mutants show an extremely tight steric contact, while results for the S2 series reveal the importance of the hydroxyl side chain, along with results indicating a highly permissible steric effect. This information may be used to aid in the design of more potent hGOAT inhibitors.

EXAMPLE

An assay for human ghrelin O-acyltransferase activity was performed using hGOAT expressed from insect (Sf9) cells using standard baculoviral methods and a fluorescent 6-mer peptide synthesized by a single step reaction followed by high performance liquid chromatography (HPLC) purification. The assay was performed at room temperature using hGOAT membrane protein, octanoyl-CoA, a fluorescent ghrelin peptide, a buffer, and a detergent. Activity may be measure by detecting the presence of any octanoylation of the ghrelin peptide. For example, the presence of octanoylated ghrelin peptide may be confirmed by HPLC or by using a fluorescent system whose fluorescence will increase as a result of octanoylation of the ghrelin peptide.

What is claimed is:

1. A substrate for use in an assay for ghrelin acylation, comprising:
an isolated peptide having the sequence selected from the group consisting of SEQ. ID NO: 4 and SEQ. ID NO: 5.

2. The substrate of claim 1, further comprising a fluorophore selected from the group consisting of acrylodan, dansyl, dapoxyl, and coumarin coupled to a cysteine residue of the isolated peptide.

3. An assay for ghrelin acylation, comprising:
an isolated peptide having the sequence selected from the group consisting of SEQ. ID NO: 4 and SEQ. ID NO: 5; and
a quantity of human ghrelin O-acyltransferase.

4. The substrate of claim 3, further comprising a fluorophore selected from the group consisting of acrylodan, dansyl, dapoxyl, and coumarin coupled to a cysteine residue of the isolated peptide.

5. A method for detecting whether a target substance inhibits human ghrelin O-acyltransferase, comprising the steps of:

providing a substrate comprising an isolated peptide having the sequence selected from the group consisting of SEQ. ID NO: 4 and SEQ. ID NO: 5;
providing a quantity of human ghrelin O-acyltransferase;
providing a quantity of said target substance; and
observing any change in production of the octanoylated product peptide.

6. The method of claim 5, wherein the step of observing any change in the production of the octanoylated product peptide comprising performing high performance liquid chromatography.

7. The method of claim 5, wherein the step of observing any change in the production of the octanoylated product peptide comprises detecting a change in fluorescence representative of the production of the octanoylated product peptide.

8. The method of claim 5, wherein the substrate further comprises a fluorophore selected from the group consisting of acrylodan, dansyl, dapoxyl, and coumarin coupled to a cysteine residue of the isolated peptide.

* * * * *

SEQUENCE LISTING

```
<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: fragment of human ghrelin peptide

<400> SEQUENCE: 1

Gly Ser Ser Phe Leu Ser
1               5

<210> SEQ ID NO 2
<211> LENGTH: 6
<212> TYPE: PRT
<213> ORGANISM: Artificial Sequence
<220> FEATURE:
<223> OTHER INFORMATION: labelled fragment of human ghrelin peptide

<400> SEQUENCE: 2

Gly Ser Ser Phe Leu Ser
1               5

<210> SEQ ID NO 3
<211> LENGTH: 6
```

```
<212> TYPE: PRT
<213> ORGANISM: Artificial Sequence
<220> FEATURE:
<223> OTHER INFORMATION: labelled human ghrelin mimic

<400> SEQUENCE: 3

Gly Cys Ser Phe Leu Ser
1               5

<210> SEQ ID NO 4
<211> LENGTH: 6
<212> TYPE: PRT
<213> ORGANISM: Artificial Sequence
<220> FEATURE:
<223> OTHER INFORMATION: labelled human ghrelin mimic

<400> SEQUENCE: 4

Gly Ser Ser Phe Cys Ser
1               5

<210> SEQ ID NO 5
<211> LENGTH: 6
<212> TYPE: PRT
<213> ORGANISM: Artificial Sequence
<220> FEATURE:
<223> OTHER INFORMATION: labelled human ghrelin mimic

<400> SEQUENCE: 5

Gly Ser Ser Phe Leu Cys
1               5

<210> SEQ ID NO 6
<211> LENGTH: 5
<212> TYPE: PRT
<213> ORGANISM: Artificial Sequence
<220> FEATURE:
<223> OTHER INFORMATION: labelled human ghrelin peptide fragment

<400> SEQUENCE: 6

Ser Ser Phe Leu Cys
1               5
```